(12) United States Patent
Hamdan

(10) Patent No.: US 8,285,374 B2
(45) Date of Patent: *Oct. 9, 2012

(54) METHODS AND SYSTEMS FOR TREATING VENTRICULAR ARRHYTHMIAS

(75) Inventor: Mohamed Hussein Hamdan, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 664 days.

This patent is subject to a terminal disclaimer.

(21) Appl. No.: 12/393,014

(22) Filed: Feb. 25, 2009

(65) Prior Publication Data

US 2010/0217343 A1    Aug. 26, 2010

(51) Int. Cl.
*A61N 1/372* (2006.01)
(52) U.S. Cl. ............ 607/4; 607/5; 607/7; 607/9; 607/14; 607/18
(58) Field of Classification Search .............. 607/4, 5, 607/7, 9, 14, 18
See application file for complete search history.

(56) References Cited

U.S. PATENT DOCUMENTS

| 5,184,615 | A | 2/1993 | Nappholz et al. |
| 7,206,633 | B2 | 4/2007 | Saba |
| 2003/0204209 | A1 | 10/2003 | Burnes |
| 2004/0002741 | A1 | 1/2004 | Weinberg |
| 2004/0172067 | A1 | 9/2004 | Saba |
| 2005/0149125 | A1 | 7/2005 | Kim |
| 2006/0259082 | A1 | 11/2006 | Youker et al. |
| 2007/0038255 | A1* | 2/2007 | Kieval et al. ............ 607/4 |
| 2008/0147138 | A1 | 6/2008 | Maskara et al. |
| 2008/0177340 | A1* | 7/2008 | Kim et al. ............ 607/4 |
| 2008/0200960 | A1 | 8/2008 | Libbus |

OTHER PUBLICATIONS

Hamdan, et al., "Baroreflex Gain Predicts Blood Pressure Recovery During Simulated Ventricular Tachycardia in Humans", Circulation, Jul. 27, 1999, pp. 381-386.
Smith, et al., "Reflex Control Of Sympathetic Activity During Simulated Ventricular Tachycardia in Humans", Circulation, Aug. 10, 1999, pp. 628-634.
Hamdan, et al., "Effect of P-Wave Timing During Supraventricular Tachycardia on the Hemodynamic and Sympathetic Neural Response", Circulation, Jan. 2-9, 2001, pp. 96-101.
Wasmund, et al., "Modulation of the Sinus Rate During Ventricular Fibrillation", Journal of Cardiovascular Electrophysiology, Feb. 2009, pp. 187-192, vol. 20, No. 2.

* cited by examiner

*Primary Examiner* — Joseph Dietrich
(74) *Attorney, Agent, or Firm* — McDermott Will & Emery LLP; James W. Hill

(57) ABSTRACT

The disclosure includes methods and systems for treating ventricular arrhythmias. Embodiments include an implantable cardiac device or system including a determining module that determines a value of a parameter indicative of a rate of an intrinsic pacemaker of a heart of a patient experiencing fast ventricular arrhythmia (FVA) and a delivery module, programmed to deliver therapy for ventricular arrhythmias to a patient. Some methods include determining a value of a parameter indicative of a rate of an intrinsic pacemaker of a heart of a patient experiencing an FVA; if the value indicates the rate is about equal to or higher than a threshold, delivering a first therapy to the patient for terminating the FVA, and if the value indicates the rate is lower than the threshold, delivering a second therapy, different from the first therapy, to the patient for terminating the FVA.

18 Claims, 15 Drawing Sheets

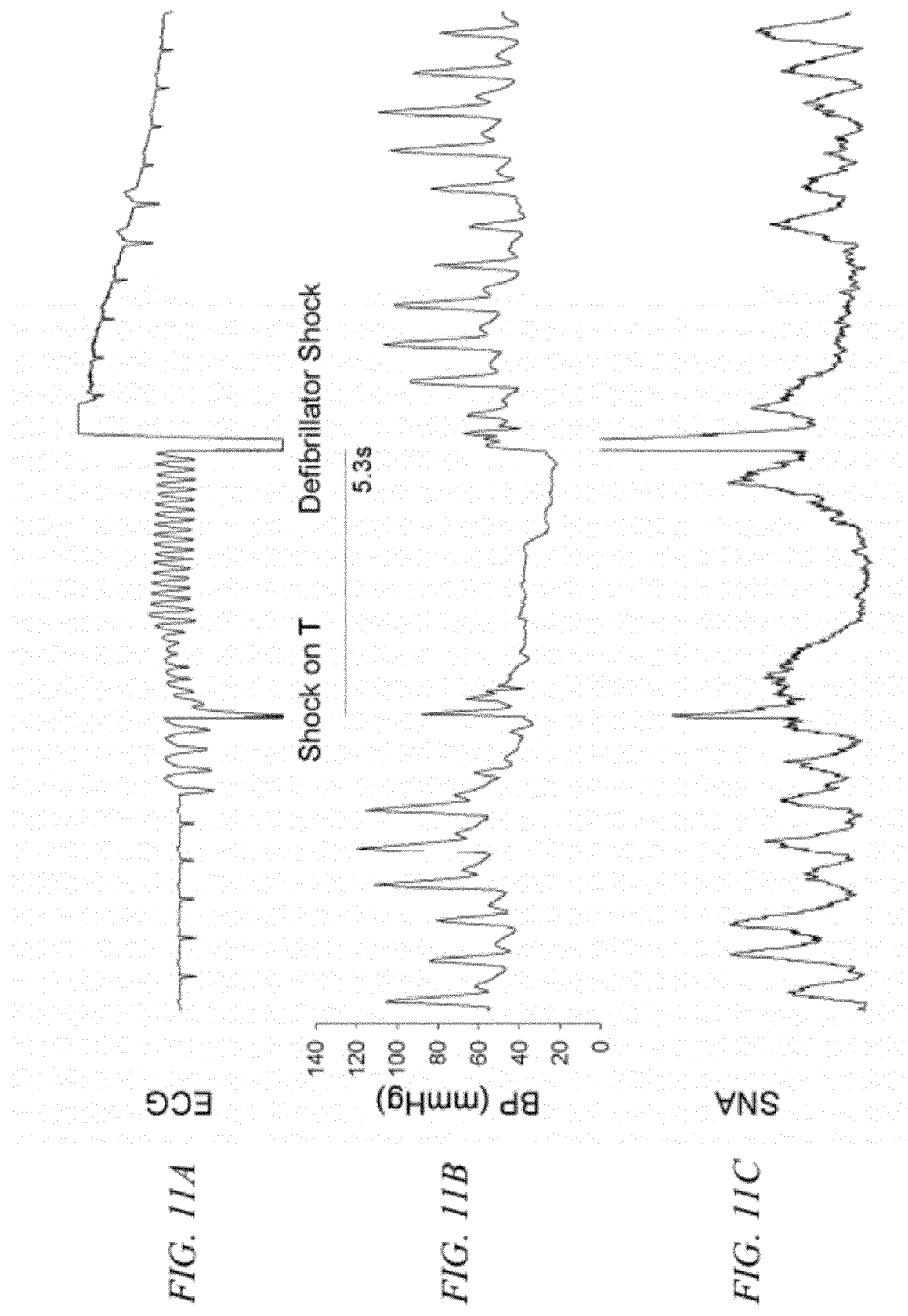

METHODS AND SYSTEMS FOR TREATING VENTRICULAR ARRHYTHMIAS

FIELD OF THE INVENTIONS

The disclosure relates generally to systems and methods for cardiac complications, and in particular to systems and methods for treating cardiac arrhythmias.

BACKGROUND OF THE INVENTION

Cardiac defibrillators are medical devices for treating patients who have experienced an episode of ventricular tachycardia or ventricular fibrillation. Cardiac defibrillators are often implanted within a patient to detect and treat ventricular tachycardia or ventricular fibrillation. Implantable cardioverter-defibrillators (ICDs) include a small battery-powered electrical impulse generator that is implanted in patients who are at risk of ventricular fibrillation. The ICDs are programmed to detect cardiac arrhythmia and correct it by delivering a jolt of electricity through electrodes that are introduced into the heart.

ICDs can keep a record of the heart's activity when an abnormal heart rhythm occurs. With this information, an electrophysiologist can study the heart's activity and ask about other symptoms that may have occurred. Sometimes the ICD can be programmed to pace the heart to restore its natural rhythm.

SUMMARY OF THE INVENTION

Described herein are systems and methods for treating cardiac arrhythmias. Some embodiments described herein relate to a method of treating a fast ventricular arrhythmia that includes determining a value of a parameter indicative of a rate of an intrinsic pacemaker of a heart of a patient experiencing a fast ventricular arrhythmia (FVA); if the value indicates the rate is about equal to or higher than a threshold, delivering a first therapy to the patient for terminating the FVA; and if the value indicates the rate is lower than the threshold, delivering a second therapy, different from the first therapy, to the patient for terminating the FVA.

In some embodiments, the rate is a depolarization rate. In some embodiments, the intrinsic pacemaker comprises the sinoatrial node of the patent. In certain embodiments, the parameter indicative of the rate comprises a sinus node cycle length. Some embodiments provide that the fast ventricular arrhythmia comprises ventricular tachycardia, and the ventricular tachycardia can has a cycle length equal to or less than about 240 ms.

In some embodiments, determining a value of a parameter indicative of a rate comprises analyzing an atrial electrogram of the patient. Some embodiments provide that determining a value of a parameter indicative of a rate is performed using an electrode positioned in the patient's heart. In certain embodiments, determining a value of a parameter indicative of a rate is performed using an electrode positioned in an atrium of the patient.

Some embodiments provide that the first therapy comprises a therapy that is relatively painless to the patient. In some embodiments, the first therapy comprises anti-tachycardia pacing. In some embodiments, the second therapy comprises at least one of defibrillation and electrical cardioversion. Some embodiments provide that the second therapy comprises defibrillation. In some embodiments, the first therapy comprises anti-tachycardia pacing, and the second therapy comprises at least one of defibrillation and electrical cardioversion.

In some embodiments, determining a value of a parameter indicative of a rate and the delivering steps, mentioned above, are performed by a device implanted in the patient. In some embodiments, wherein the parameter indicative of a rate comprises a sinus node cycle length. The first therapy can include anti-tachycardia pacing, and the second therapy can include at least one of defibrillation and electrical cardioversion. The determining a value of a parameter indicative of a rate and the delivering steps can be, with the above description, performed by a device implanted in the patient.

In some embodiments, if the value indicates the rate is lower than a threshold, some methods provide for delivering a third therapy that stimulates the patient's sympathetic nervous system. In certain embodiments, the third therapy is sufficient to raise an arterial blood pressure in the patient. Some embodiments provide that the third therapy is electrical. In some embodiments, the third therapy comprises delivery of a sympathetic or sympathomimetic agent to the patient.

Some embodiments, provide a method, of treating a fast ventricular arrhythmia, including determining a value of a parameter indicative of at least one of vagal activity and peripheral sympathetic activity in a patient experiencing a fast ventricular arrhythmia; if the value is in a range indicating the ventricular arrhythmia is more likely to terminate in response to a painless therapy than if the value is outside the range, delivering the painless therapy to the patient; and if the value is outside the range, delivering a second therapy, comprising least one of defibrillation and electrical cardioversion, to the patient.

In some embodiments, the painless therapy comprises anti-tachycardia pacing. Some embodiments provide that the determining a value of a parameter and the delivering steps are performed by a device implanted in the patient. In some embodiments, the parameter comprises an indicator of depolarization of an intrinsic pacemaker in the patient's heart. Some embodiments provide that the intrinsic pacemaker comprises the sinoatrial node of the patient. Some embodiments provide that the parameter indicative of the rate comprises a sinus node cycle length.

In some embodiments, determining a value of a parameter comprises analyzing an atrial electrogram of the patient. Some embodiments provide that the determining a value of a parameter is performed using an electrode positioned in the patient's heart. In some embodiments, determining a value of a parameter is performed using an electrode positioned in an atrium of the patient.

Some embodiments provide that the second therapy of the above-mentioned embodiments comprises defibrillation. In some embodiments, the parameter comprises a sinus node cycle length and the determining a value of a parameter and the delivering steps are performed by a device implanted in the patient.

Some embodiments describe an implantable cardiac device or system, for treating a fast ventricular arrhythmia. In some embodiments, the device and/or system can include a determining module that determines a value of a parameter indicative of a rate of an intrinsic pacemaker of a heart of a patient experiencing a fast ventricular arrhythmia (FVA) and a delivery module, programmed to deliver a first therapy for terminating the FVA to the patient if the value indicates the rate is about equal to or higher than a threshold, and to deliver a second therapy for terminating the FVA, different from the first therapy, to the patient if the value indicates the rate is lower than the threshold.

In some embodiments, the rate is a depolarization rate. In some embodiments, the parameter is indicative of a rate of the sinoatrial node of the patent. Some embodiments provide that the parameter comprises a sinus node cycle length. In some embodiments, at least one of the first and second therapies is electrical. In some embodiments, the determining module analyzes an atrial electrogram of the patient, and in some embodiments, the determining module uses information derived from a signal transmitted via an electrode, positioned in an atrium of the patient, to determine the parameter value.

Some embodiments of the device and/or system provide that the first therapy comprises anti-tachycardia pacing, and some embodiments provide that the second therapy comprises at least one of defibrillation and electrical cardioversion. In some embodiments, the second therapy comprises defibrillation. In certain embodiments, the first therapy comprises anti-tachycardia pacing, and the second therapy comprises defibrillation.

In certain embodiments, a method, of treating a fast ventricular arrhythmia, is described including determining a value of a parameter indicative of a rate of an intrinsic pacemaker of a heart of a patient experiencing a fast ventricular arrhythmia (FVA); if the value indicates the rate is about equal to or higher than a threshold, delivering an electrical therapy, having a first value of a therapy parameter, to the patient for terminating the FVA; and if the value indicates the rate is lower than the threshold, delivering the electrical therapy, having a second value of the therapy parameter, to the patient.

In some embodiments, the rate is a depolarization rate. In some embodiments, the therapy parameter comprises at least one of a pulse waveform, a pulse rate, a pulse amplitude, a pulse width, and a pulse interval. In certain embodiments, the intrinsic pacemaker comprises the sinoatrial node of the patient. In some embodiments, the parameter indicative of the rate comprises a sinus node cycle length. Some embodiments provide that the fast ventricular arrhythmia comprises ventricular tachycardia. In some embodiments, the ventricular tachycardia has a cycle length equal to or less than about 240 ms.

In some embodiments, determining a value of a parameter indicative of a rate of an intrinsic pacemaker comprises analyzing an atrial electrogram of the patient. In certain embodiments, determining a value of a parameter indicative of a rate of an intrinsic pacemaker is performed using an electrode positioned in the patient's heart. Some embodiments provide that determining a value of a parameter indicative of a rate of an intrinsic pacemaker is performed using an electrode positioned in an atrium of the patient.

In some embodiments, the first therapy comprises a therapy that is relatively painless to the patient. Some embodiments provide that the first therapy comprises anti-tachycardia pacing. In certain embodiments, the second therapy comprises at least one of defibrillation and electrical cardioversion. In some embodiments, the second therapy comprises defibrillation. In certain embodiments, the first therapy comprises anti-tachycardia pacing, and the second therapy comprises defibrillation. Some embodiments provide that determining a value of a parameter indicative of a rate of an intrinsic pacemaker and the delivering steps are performed by a device implanted in the patient.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

General descriptions provided herein that implement various features of the disclosure will now be described with reference to the drawings. The drawings and the associated descriptions are provided to illustrate embodiments of the disclosure and not to limit the scope of the disclosure.

FIG. 11A depicts ECG recordings during VF induction in a patient undergoing an ICD implant.

FIG. 11B depicts BP recordings during VF induction in a patient undergoing an ICD implant.

FIG. 11C depicts SNA recordings during VF induction in a patient undergoing an ICD implant.

DESCRIPTION OF THE INVENTIONS

Figure 1:
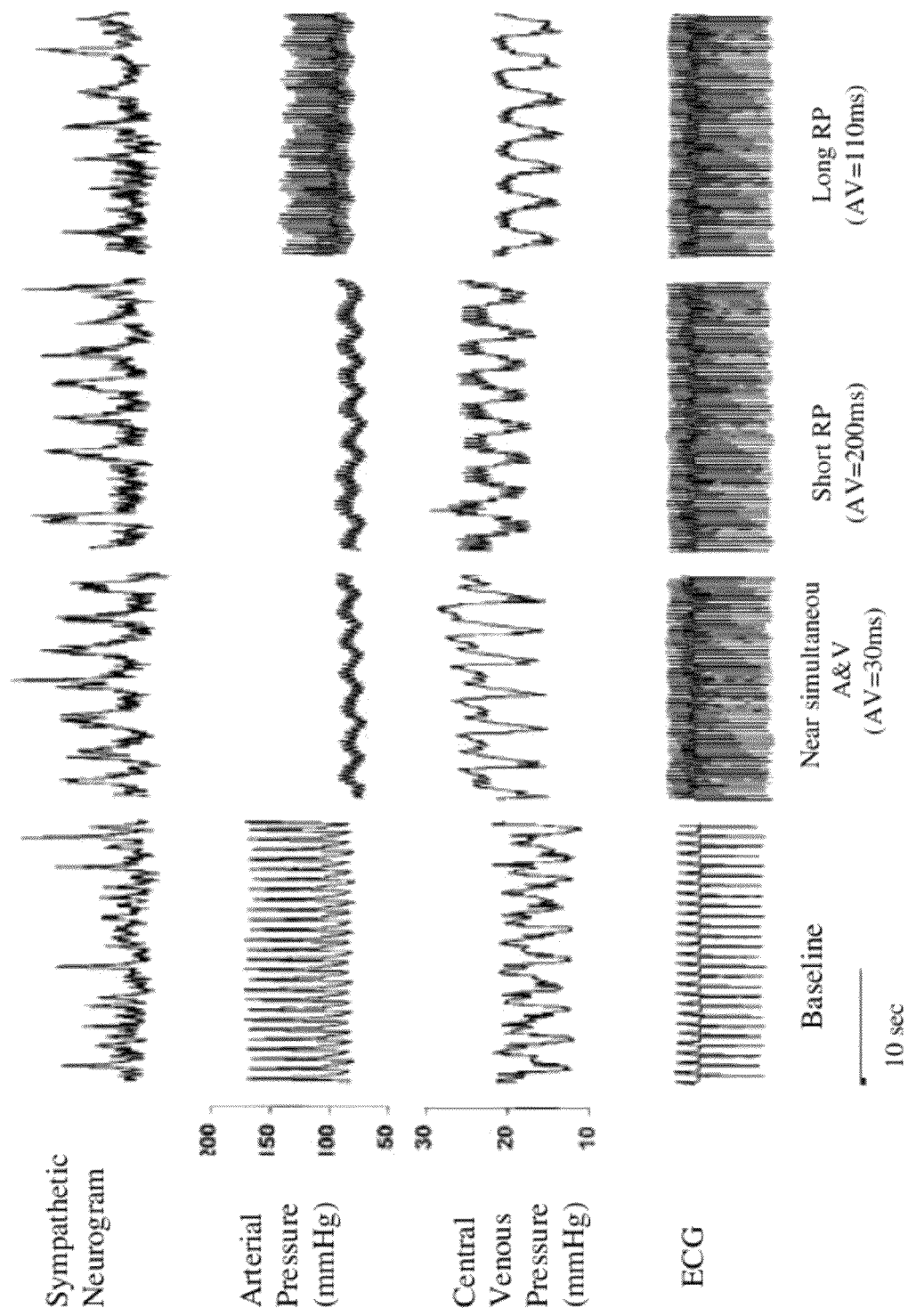
FIG. 1 depicts sample tracings of integrated sympathetic neurogram, arterial blood pressure, central venous pressure, and electrocardiogram during baseline and during rapid pacing in accordance with embodiments described herein.

The present disclosure provides systems and methods for treating cardiac arrhythmias. Some embodiments include an implantable cardiac device or system, for treating a fast ventricular arrhythmia. Certain embodiments can include a determining module that determines a value of a parameter indicative of a rate of an intrinsic pacemaker of a heart of a patient experiencing FVA. In some embodiments, for example, the rate can be a depolarization rate. Certain embodiments can include a delivery module, programmed to deliver a plurality of therapies to a patient experiences cardiac arrhythmia. A first therapy can be delivered, for terminating the FVA, to the patient if the value indicates the rate is about equal to or higher than a threshold. A second therapy, different from the first therapy, can be delivered to the patient if the value indicates the rate is lower than the threshold.

Some embodiments relate to a method of treating a fast ventricular arrhythmia that includes the step of determining a value of a parameter indicative of a rate of an intrinsic pacemaker of a heart of a patient experiencing a fast ventricular arrhythmia (FVA). In some embodiments, the rate is a depolarization rate. The method can provides treatment for a patient based on whether the rate is within a threshold or beyond such threshold. If the value indicates the rate is about equal to or higher than the threshold, the method provides for delivering a first therapy to the patient for terminating the FVA. If the value indicates the rate is lower than the threshold, the method provides for delivering a second therapy, different from the first therapy, to the patient for terminating the FVA.

In some embodiments, if the value indicates the rate is lower than a threshold, some methods provide for delivering a third therapy that stimulates the patient's sympathetic nervous system. In certain embodiments, the third therapy is sufficient to raise an arterial blood pressure in the patient. Some embodiments provide that the third therapy is electrical. In some embodiments, the third therapy comprises delivery of a sympathetic or sympathomimetic agent to the patient. In some embodiments, the third therapy is a combination of electrical and delivery of a sympathetic or sympathomimetic agent to the patient. In some embodiments, the agent may be delivered through an electrode that may be used for diagnostic or therapeutic purposes. Examples of additional drug delivery methods are know in the art and may be implemented accordingly. Examples of agents that can be used include epinephrine, isoproterenol, dobutamine, etc.

In most circumstances, the application of painless therapy to fast ventricular arrhythmias (FVA; e.g., Cycle Length (CL) <240 ms) is limited by the inability to predict who is able to tolerate the arrhythmia without loss of consciousness. Described herein are tools to predict blood pressure response during FVA, thus enabling the application of painless therapy in patients who can tolerate it.

During simulated ventricular tachycardia (e.g., CL 240 ms), the arterial baroreflex plays a major role in mediating the sympathetic changes with minimal contribution from the cardiopulmonary baroreflex (Circulation. 1999 Aug. 10; 100(6): 628-34 (incorporated herein by reference)). Arterial baroreflex gain correlates with the blood pressure response (Circulation. 1999 Jul. 27; 100(4):381-6 (incorporated herein by reference)). In follow-up studies aimed at evaluating the role of the baroreflex in ventricular fibrillation (e.g., CL<240 ms), no correlations were found between arterial baroreflex gain and the changes in sinus node cycle length (SNCL). SNCL did not change and even lengthened in some patients, suggesting vagal activation and/or sympathoinhibition.

It has been observed that peripheral sympathetic activity decreased during induced ventricular fibrillation in a small number of patients. The lack of change, and even lengthening of the SNCL, combined with the finding of sympathoinhibition suggested that, in some patients, a "vasovagal"-like reaction could be taking place. During a vasovagal reaction, a paradoxical response occurs resulting in heart rate slowing, i.e., SNCL lengthening and sudden vasodilatation leading to a decrease in blood pressure. If this paradoxical response were to occur during FVA, the blood pressure response would be different in those with a vasovagal reaction when compared to those without a vasovagal reaction. By assessing the SNCL changes during the arrhythmia might, it is possible to get an indication as to who will have a greater decrease in blood pressure and thus potentially loss of consciousness. The application of painless therapy in patients who develop of a vasovagal reaction might be dangerous since they are more prone to lose consciousness. However, its use in patients without a vasovagal reaction might be beneficial, in that additionally treatment methodologies can be implemented. In some of these patients, successful painless therapy will prevent the delivery of painful shocks, thus improving the quality of life of thousands of patients with implantable defibrillators.

In conducting analysis of the possible "vasovagal" reaction it was found that found that: 1) SNCL did not change and even lengthened in a small number of animals; 2) the mechanism of the SNCL changes appeared to be vagally mediated; and 3) the percent decrease in blood pressure was greater in the animals with no SNCL changes or SNCL lengthening when compared to those with SNCL shortening. These findings were made from a limited number of studies.

It is also possible to distinguish patients without vasovagal reaction, i.e., those with SNCL shortening, by assessing the magnitude of the change in SNCL. The greater the SNCL shortening, the lesser the decrease in blood pressure, thus further improving the algorithm for painless therapy. No algorithm in place uses a device data to predict blood pressure response during ventricular arrhythmias. This disclosure will highlight what information should be looked at, and more importantly, will provide guidelines on how to use it in thousands of patients with devices.

Shock therapy has a major impact on the quality of life of thousands of patients with implantable defibrillators. While painless therapy has been shown to be effective in the treatment of ventricular arrhythmias with, for example, CL greater than about 240 ms, its application in the treatment of rapid ventricular arrhythmias with, for example, CL less than about 240 ms has been limited. The major concern has been the incidence of syncope. Proposed herein are new methods and systems that enable the identification of patients who can better tolerate painless therapy.

Simulated VT is associated with an increase in sympathetic nerve activity (SNA), and the magnitude of sympathoexcitation is correlated with arterial baroreflex gain. SNA recordings are not obtained in patients during VF. In addition, the relationship between sinus node cycle length (SNCL) changes, and SNA during VF has not been evaluated.

In some methods, patients receiving dual chamber ICD implants with defibrillation threshold testing were asked to enroll. SNA recordings were attempted in all patients. In addition, the mean SNCL was measured during the 5 seconds preceding VF onset and the last 5 seconds before defibrillation. Seven patients were enrolled, and SNA measurements were successfully obtained in 3 patients. Atrial recordings were available in 6 patients. In patients with successful SNA recordings, sympathoinhibition was observed during VF in 2 patients, with sympathoexcitation noted in the remaining patient. Compared to baseline, SNCL shortened in 4 patients (−14% from baseline) and lengthened in the remaining 2 patients (+2% from baseline). In those with successful SNA recordings and SNCL measurements, the increase and decrease in SNA was associated with a reduction and lengthening in SNCL. These findings of sympathoinhibition associated with SNCL lengthening suggest the presence of vasovagal-like physiology during VF in a subgroup of patients. The implications regarding the magnitude of BP fall and application of painless therapy remain to be evaluated.

It has been shown in humans and in a porcine model that sinus node cycle length (SNCL) increases during VF in a significant number of cases, although it is uncertain what mechanism is responsible for the SNCL changes during VF. In eight anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 seconds before applying a DC shock. Following a 10 minute recovery period, atropine (A, n=2) at 0.04 mg/kg, propranolol (P, n=2) at 0.2 mg/kg, both (A+P, n=2) or neither (Placebo, n=2) were administered at random, and VF was re-induced. SNCL changes were assessed before and after drug/placebo administration. Percent SNCL change (%ΔSNCL) was defined as %ΔSNCL=(VF-SNCL−Baseline-SNCL)/(Baseline-SNCL)*100. Atropine administration reversed the SNCL lengthening observed during VF while propranolol had little or no effect on SNCL shortening (see FIG. 9). The SNCL changes during the first 30 seconds of VF appear to be vagally mediated. The relationship between SNCL changes and peripheral sympathetic activity remain uncertain.

It has been shown that sinus node cycle length (SNCL) increases during VF in a significant number of cases. The relationship between SNCL changes and systemic BP remain unknown. In specific, whether SNCL lengthening is associated with peripheral sympathoinhibition and a greater decrease in BP, i.e., a vasovagal-like reaction is unclear. In test involving eleven anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 seconds before applying a DC shock. Animals were divided in to 2 groups based on SNCL response during VF: Shortening group (n=7, %ΔSNCL=−17%), Lengthening group (n=4, %ΔSNCL=4%). RESULTS: In the Shortening group, mean BP fell by 53% in the first 10 sec. when compared to NSR and continued to fall to 64% and 68% at 20 sec. and 30 sec., respectively. In the Lengthening group, BP fell by 72%, 81% and 83% when compared to baseline. The differences in percent decrease in BP between the groups were statistically significant at all 3 time points during VF ($p<0.05$). SNCL lengthening was associated with a greater decrease in BP when compared to SNCL shortening. The above findings suggest that SNCL changes during VF might be helpful in predicting the magnitude of the hemodynamic fall in BP. Such information could be useful in deciding who has "time" for painless therapy before delivering shock therapy in patients with dual chamber ICDs.

Figure 10A:
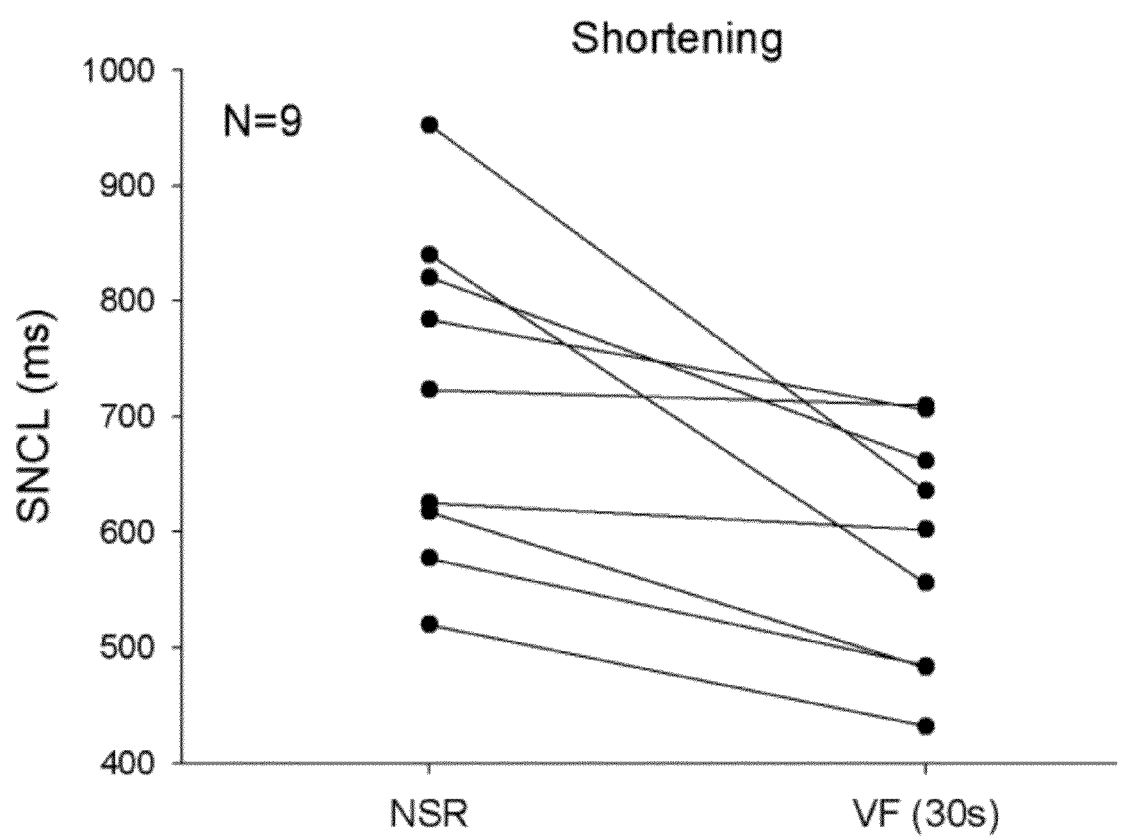
FIG. 10A depicts results of changing SNCL, compared to VF induction (NSR), and during a 30-second period of AF, in which the SNCL decreased.
Figure 10B:
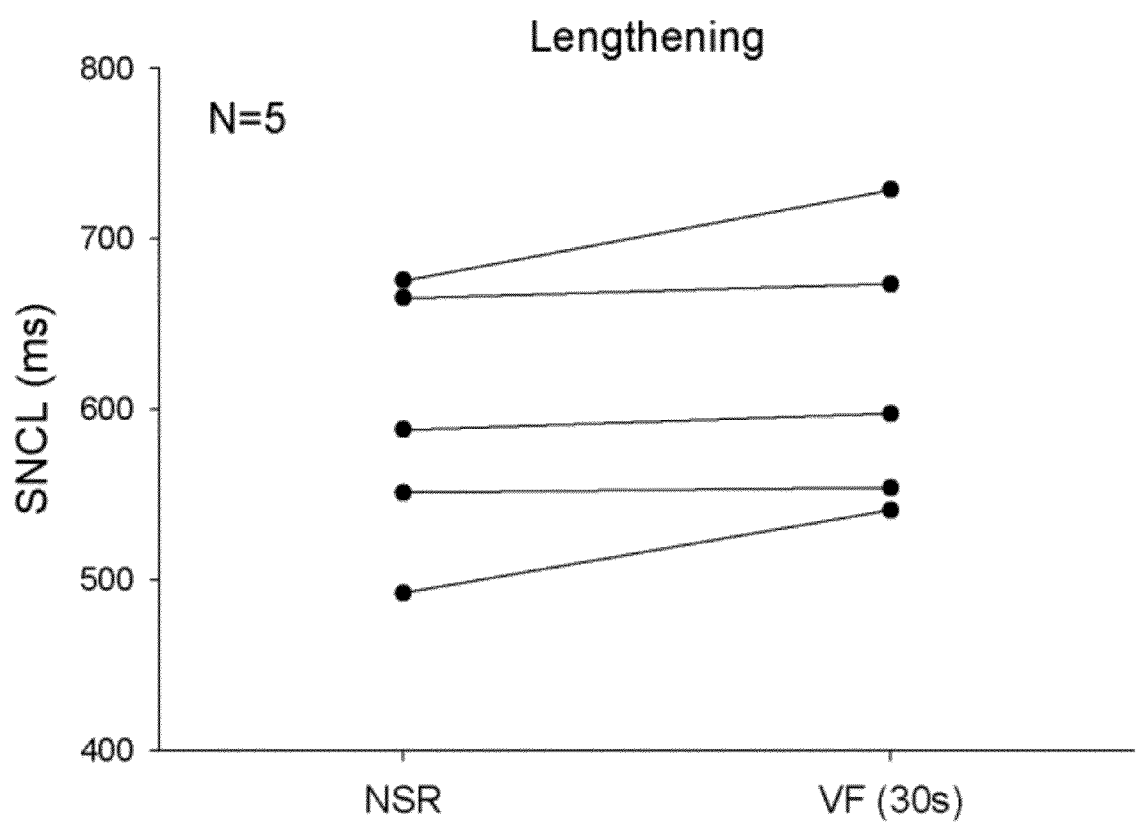
FIG. 10B depicts results of changing SNCL, compared to NSR, and during a 30-second period of AF, in which the SNCL increased.

While some studies have evaluated the autonomic changes prior to VF onset, the changes during VF remain poorly understood. Analysis of the SNCL changes during VF provides a unique opportunity to assess the autonomic changes. In fourteen anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 seconds before applying DC shock. Mean SNCL was measured during the 10-second period prior to VF induction (NSR) and during the 30-second period of VF. Compared to NSR, SNCL during VF shortened in 9 animals and lengthened in 5 (36%), (see FIGS. 10A and 10B). As a group, the percent change in SNCL during the first 10-sec interval was greater than the percent change during the second and third 10-sec. intervals. Similarly, the percent change during the second 10-sec. interval was greater than the percent change in the third 10-sec interval. SNCL lengthening was observed in 36% of the pigs during the first 30 seconds of VF suggesting increased vagal tone or decreased sympathetic activity in one third of the cases. In addition, there was a gradual increase in SNCL regardless of the magnitude or direction of the initial change. The underlying mechanism of the SNCL changes and the clinical implications remain unknown.

The role of the baroreflex system in various tachyarrhythmias has been the subject of extensive research. During tachyarrhythmias, arterial blood pressure (BP) decreases while central venous pressure (CVP) increases. On one hand, the unloading of the arterial baroreceptors results in an increase in sympathetic nerve activity (SNA) and vagal inhibition via the arterial baroreflex. On the other hand, the increase in filling pressures results in a decrease in SNA and an increase in vagal tone via the cardiopulmonary baroreflex. These competing reflexes result in mixed messages to the central nervous system. It has been shown that during supraventricular and ventricular tachycardia, the arterial baroreflex predominates with minimal contribution from the cardiopulmonary reflex. Indeed, the net response during these tachycarrhythmias is a state of sympathoexcitation, which has been shown to correlate with blood pressure recovery. While the autonomic changes during supraventricular and ventricular tachycardia have been described, the responses during fast ventricular arrhythmias (FVA: VF and rapid VT with about CL<240 ms) remain unknown.

Assessment of the autonomic changes during ventricular arrhythmias is a challenge as the surface ECG prohibits the evaluation of sinus node function. Thus far, human studies have used microneurography as the only direct method for assessing the sympathetic changes during tachyarrhythmias. With the increased number of defibrillator implants incorporating atrial leads, analysis of the changes in sinus node cycle length (SNCL) from atrial electrograms recorded provides a unique opportunity to assess the autonomic changes that accompany these arrhythmias. We have recently shown in defibrillator patients that SNCL shortening during ventricular tachycardia, a marker of the degree of sympathoexcitation, was a predictor of successful anti-tachycardia pacing. Reflex sympathoexcitation is known to improve conduction and shorten ventricular refractory period, thus increasing the likelihood that a pacing impulse reaches the excitable gap and collides both orthodromically and antidromically with the tachycardia wavefront. In another study, we assessed whether the changes in SNCL during VF correlated with arterial baroreflex gain (BRG). BRG and SNCL measurements were successfully obtained in 18 patients undergoing the implantation of an implantable cardiovertor defibrillator (ICD). During VF, SNCL shortened in 11 patients and surprisingly lengthened in 7 patients. We found no correlation between arterial BRG and percent change in SNCL. To our knowledge, the mechanisms underlying the SNCL changes during VF and VT with CL<240 ms remain unknown.

Determination of the mechanisms responsible for the SNCL changes during FVA (VF and VT with about CL<240 ms) and its relationship to peripheral sympathetic activity would be advantageous. It is believed the changes in SNCL during FVA are vagally mediated, and that the lengthening and shortening in SNCL are associated with a decrease and an increase in peripheral sympathetic activity respectively. Accordingly, it is understood that some patients develop paradoxically a vasovagal-like reaction during FVA, and the analysis of the SNCL could help identify this subgroup of patients.

Increased sympathetic activity during ventricular tachycardia has been shown to be beneficial. Indeed, our group has shown that the greater the sympathoexcitation was during ventricular tachycardia, the greater was the BP recovery both during and after tachycardia termination.

It is believed that the effects of FVA (VF and VT with about CL<240 ms) on peripheral sympathetic activity have not been evaluated. In addition, the role of the autonomic changes in mediating blood response and time to symptoms remain unknown. The study described above was the first to look at the sinus rate as a surrogate of the autonomic changes that occur during VF. If the lengthening and shortening in SNCL are indeed associated with a decrease and an increase in peripheral sympathetic activity respectively, then patients with SNCL lengthening should have a greater decrease in BP due to a decrease in arteriolar resistance, and earlier onset of symptoms when compared to patients with SNCL shortening. Conversely, patients with SNCL shortening would have a lesser decrease in BP due to elevated arteriolar resistance and delayed onset of symptoms when compared to patients with SNCL lengthening.

Determination of the role of the autonomic changes during FVA in predicting blood pressure response and time to symptoms would be advantageous. It is believed that the SNCL lengthening during FVA is associated with a greater decrease in blood pressure when compared to those with SNCL shortening. Furthermore, it is believed that patients with SNCL lengthening have a shorter time to near syncope and syncope when compared to those with SNCL shortening.

The number of implantable cardioverter-defibrillators (ICD) implants per year, at the time of this disclosure, about 50,000 and is expected to grow as an aging population and expanding ICD indications intersect. A sub-study of the MADIT II ICD recipients revealed that, over an average of 17.2 months of follow-up, 24% of ICD recipients received an appropriate ICD therapy. Some ICDs, have a variety of programmable options for antitachycardia pacing (ATP), which can be an effective alternative to shocks. Despite encouraging results from studies employing ATP algorithms, the clinical predictors of successful ATP remain poorly understood. Furthermore, this therapy is rarely used for the treatment of fast ventricular arrhythmias (CL<240 ms) because of the fear of syncope should ATP fails. Therefore, gaining an insight about the BP response and time to symptoms onset during FVA should greatly enhance our utilization of this painless therapy. Indeed, ICD shocks have shown to be associated with newly diagnosed depression and anxiety disorders in addition to their impact on battery life longevity. Therefore, any decrease in the number of shocks through the utilization of successful ATP should have a great impact on the quality of life of millions of Americans with ICD implants in addition to device longevity.

Information derived from the studies discussed above are incorporated into an algorithm that uses ATP therapy in patients with FVA. As stated above, ATP is rarely used for the treatment of FVA (CL<240 ms) because of the fear of syncope should ATP fails. It is believed that the SNCL changes can provide further information on the early BP response and time to symptoms in patients with FVA. In specific, it is believed that anti-tachycardia pacing reduces shock therapy for fast ventricular arrhythmias in patients with SNCL shortening without a significant increase in acceleration or syncope.

Supraventricular tachycardias (SVT) with a 1:1 atrioventricular (AV) relationship are classified according to the location of the P wave in relation to the QRS: Short RP tachycardias (RP<PR), long RP (RP>PR) tachycardias and tachycardias with no identifiable P waves. Little is known about the significance of the P wave relation to the QRS in terms of hemodynamic and neural outcome. The effect of atrial systole timing on the hemodynamic and sympathetic neural response during rapid dual chamber pacing (DDD) was evaluated in 10 patients with a DDD pacemaker. Blood pressure, central venous pressure and sympathetic nerve activity (SNA) were recorded continuously during rapid DDD pacing at a rate of 175 bpm (CL=342 ms) with 3 AV intervals: AV=30 ms, AV=200 ms and AV=110 ms, simulating SVT with no identifiable P wave, short RP and long RP tachycardia respectively. The relationship of atrial systole to ventricular systole was found to play a major role in the hemodynamic and neural response during tachycardia, with long RP tachycardia having the most favorable response. The changes in SNA seem to parallel the changes in mean BP with no clear evidence of predominant atrial vasodepressor response.

Figure 2A:
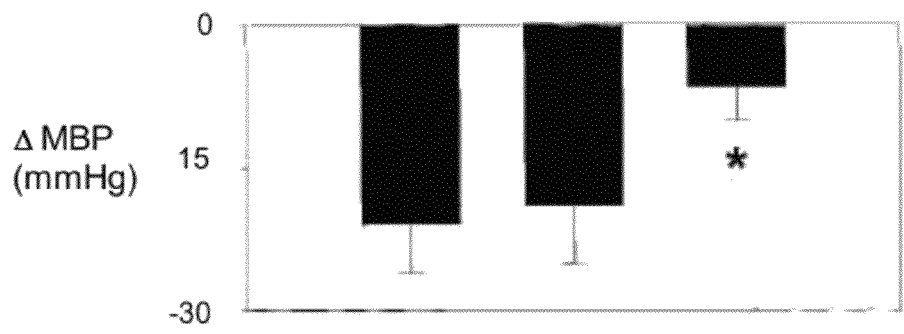
FIG. 2A depicts changes in mean blood (arterial) pressure (MBP, MAP) during pacing, in accordance with embodiments described herein, with near simultaneous atrial and ventricular systole (A&V), short-rapid pacing tachycardia, and long-rapid pacing tachycardia.
Figure 2B:
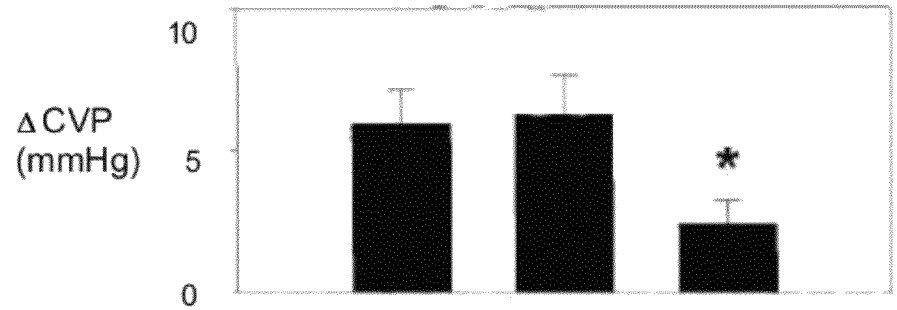
FIG. 2B depicts changes in central venous pressure (CVP) during pacing, in accordance with embodiments described herein, with near simultaneous atrial and ventricular systole (A&V), short-rapid pacing tachycardia, and long-rapid pacing tachycardia.
Figure 2C:
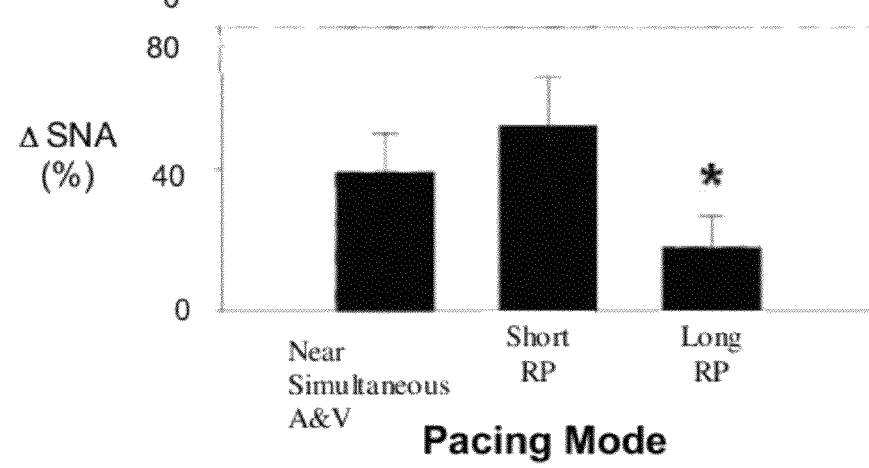
FIG. 2C depicts changes in sympathetic nerve activity (SNA) during pacing, in accordance with embodiments described herein, with near simultaneous atrial and ventricular systole (A&V), short-rapid pacing tachycardia, and long-rapid pacing tachycardia.
Figure 3A:
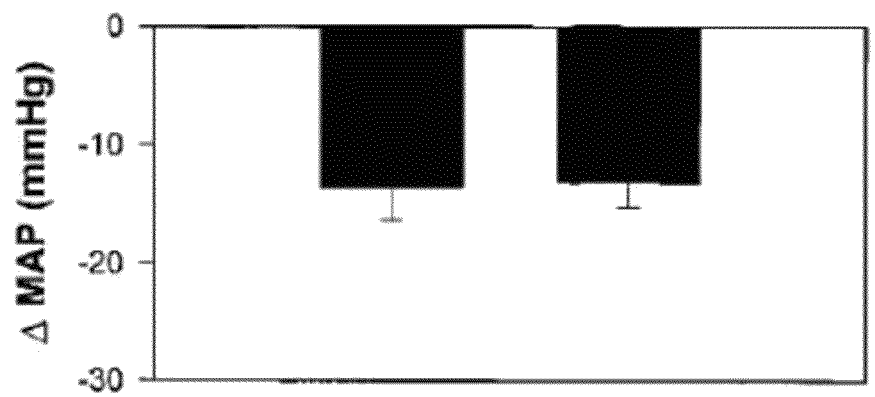
FIG. 3A depicts changes in MAP in response to pacing and nitroprusside infusion (NTP).
Figure 3B:
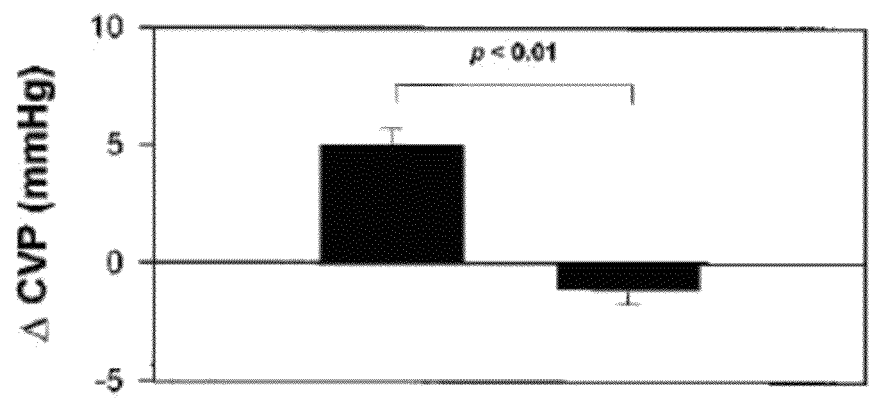
FIG. 3B depicts changes in CVP in response to pacing and nitroprusside infusion (NTP).
Figure 3C:
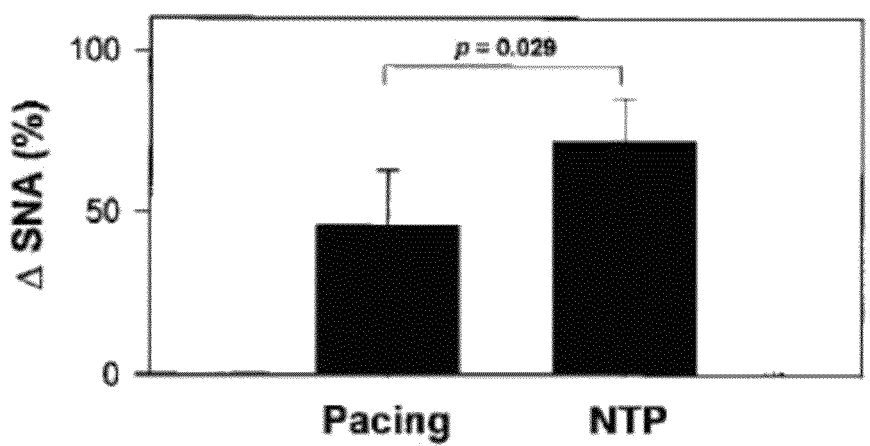
FIG. 3C depicts changes in SNA in response to pacing and nitroprusside infusion (NTP).
Figure 4:
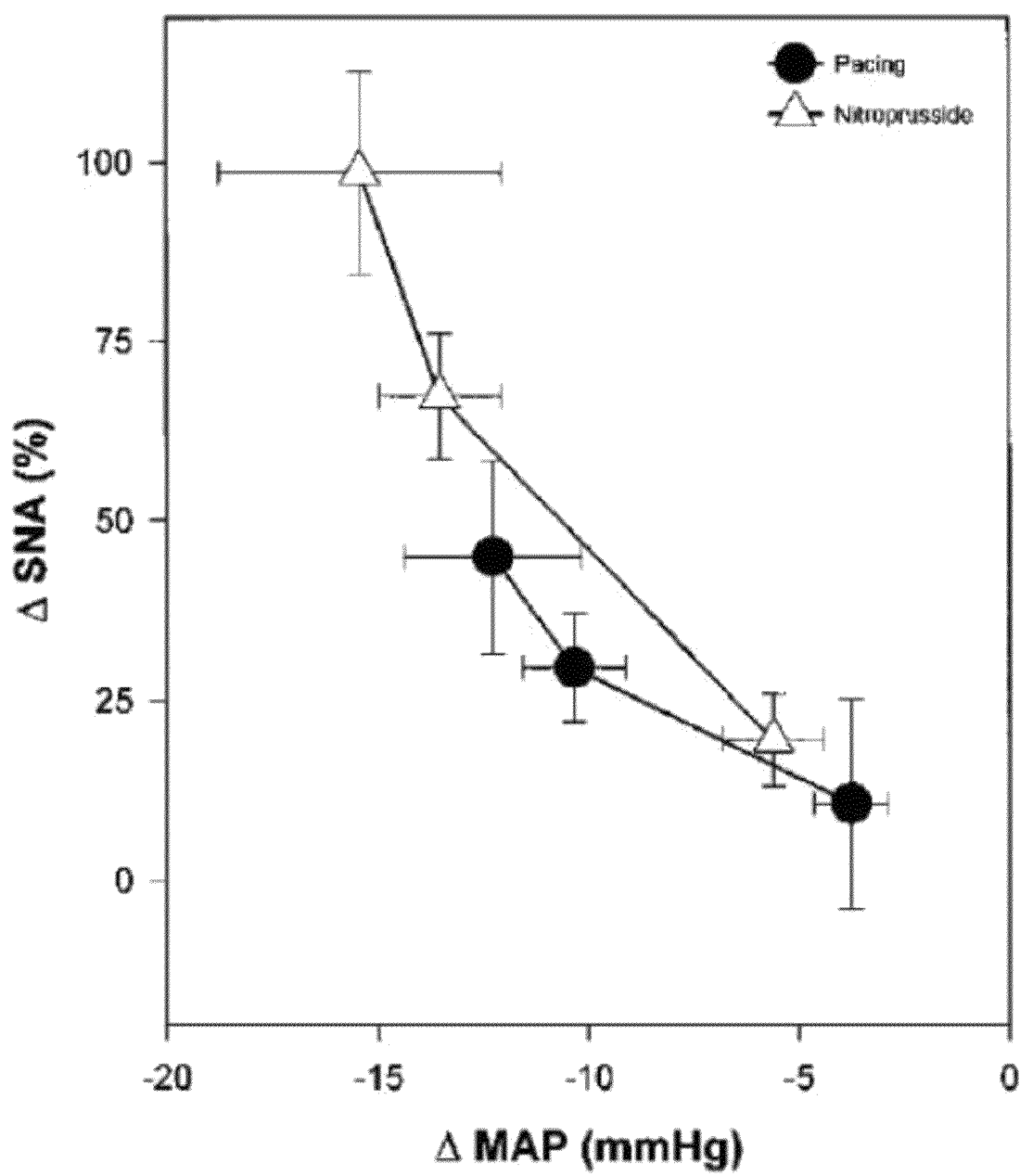
FIG. 4 depicts a chart comparing changes in MAP and SNA in response to pacing and nitroprusside infusion (NTP).

FIG. 1 depicts sample tracings of integrated sympathetic neurogram, arterial BP, CVP, and ECG during baseline (pre-pacing) and during minute 3 of rapid pacing (175 bpm) with either near-simultaneous atrial and ventricular systole (A&V), short-RP tachycardia, or long-RP tachycardia. In this individual, it is apparent that long-RP tachycardia produced a higher arterial BP, lower CVP, and less increase in SNA. FIGS. 2A-2C depict changes (mean±SEM) in MAP (DMAP), CVP (DCVP), and SNA (DSNA) during minute 3 of pacing with near simultaneous atrial and ventricular systole (A&V), short-RP tachycardia, and long-RP tachycardia. The asterisks * in FIGS. 2A-2C indicate a significant difference from the other 2 pacing modes (P<0.05).

During ventricular tachycardia, BP decreases while CVP increases. The decrease in BP is expected to result in an increase in SNA due to unloading of the arterial baroreceptors, while the increase in CVP should result in a decrease in SNA due to activation of the cardiopulmonary baroreceptors. It is believed that arterial BRG predominated in mediating the sympathetic changes with minimal contribution from the cardiopulmonary baroreceptors. Furthermore, it is believed that arterial BRG correlated with the hemodynamic outcome during sustained ventricular tachycardia. In a test, efferent post-ganglionic muscle SNA, BP and CVP were measured during ventricular pacing (3 pacing CLs) and compared to the responses to 3 doses of nitroprusside infusion (NTP). We also measured SNA, BP and CVP during VP (400 ms) under 3 conditions: 1) Pacing alone, 2) Pacing+Head-up tilt, and 3) Pacing+Phenylephrine. FIGS. 3A-3C and FIG. 4 depict mean±SEM responses to pacing and NTP that produced comparable decreases in MAP (13.6±2.7 vs 13.2±1.8 mmHg).

Figure 5A:
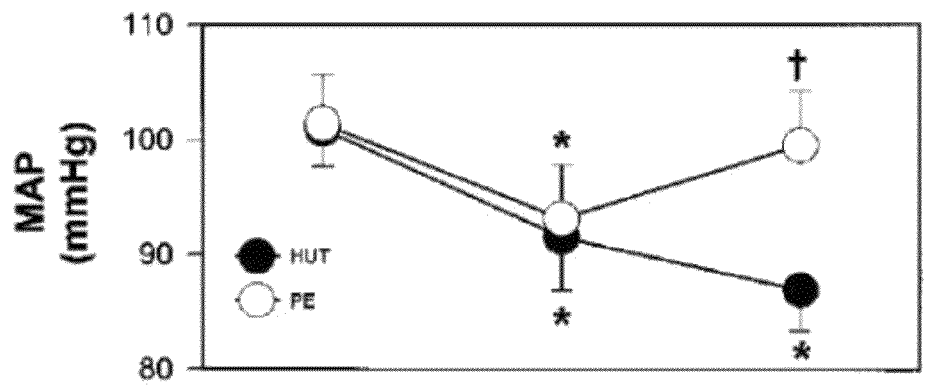
FIG. 5A depicts changes in MAP in response to ventricular pacing (VP) and VP with phynylephrine infusion (PE) or head-up tilt (HUT).
Figure 5B:
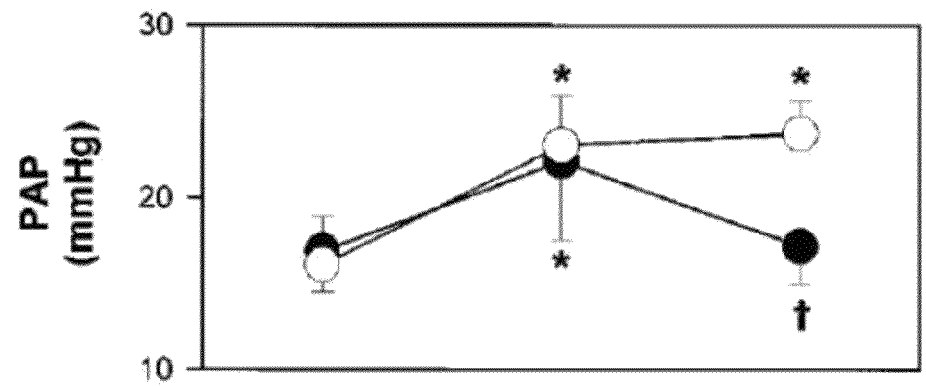
FIG. 5B depicts changes in pulmonary arterial pressure (PAP) in response to ventricular pacing (VP) and VP with phynylephrine infusion (PE) or head-up tilt (HUT).
Figure 5C:
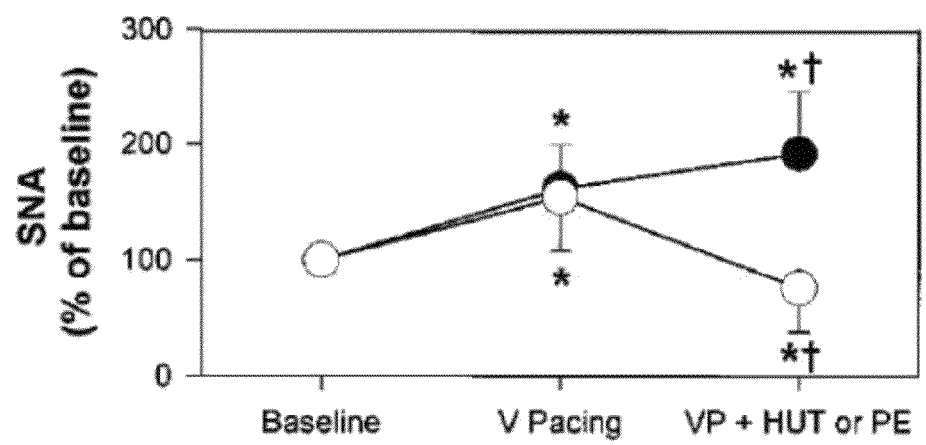
FIG. 5C depicts changes in SNA in response to ventricular pacing (VP) and VP with phynylephrine infusion (PE) or head-up tilt (HUT).

NTP resulted in a significantly greater increase in SNA when compared to VP (FIGS. 3A-3C and 4). The reason for that is that while both NTP and VP resulted in a decrease in BP and thus unloading of the arterial baroreceptors, NTP infusion was associated with a decreased in CVP while VP resulted in an increase in CVP. A decrease in CVP results in a greater increase in SNA due to unloading of the cardiopulmonary baroreceptors. On the other hand, an increase in CVP results in sympathoinhibition due to activation of the cardiopulmonary baroreceptors. The fact that VP resulted in an increase in SNA despite the increase in CVP suggests that arterial BRG predominates in mediating the SNA changes with minimal contribution form the cardiopulmonary BRG. This point is further illustrated in FIGS. 5A-5C where head-up tilt added to VP resulted in a greater increase in SNA due to the associated reduction in CVP. On the other hand, phenylephrine infusion resulted in a decrease in SNA due to the increase in BP, which was the main trigger for the increase in SNA. FIGS. 5A-5C depict summary data for MAP, PAP and SNA responses to ventricular pacing (VP) and VP with phenylephrine infusion (PE, ○) or head-up tilt (HUT, □). Mean±SEM. The * indicates a significant difference from baseline (p<0.05), and the † indicates a significant difference from VP alone.

Figure 6:
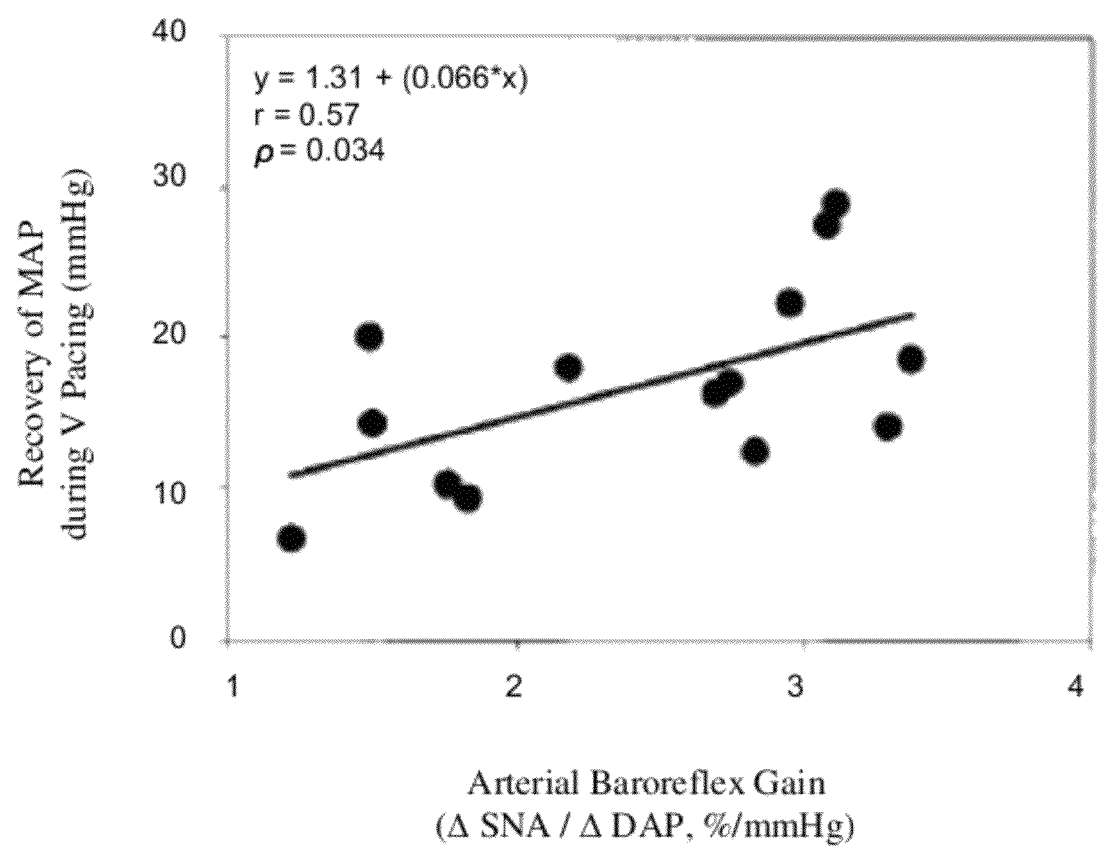
FIG. 6 depicts a relationship of recovery of MAP during VP to artieral baroreflex sympathetic gain estimated during NTP infusion.

To test the proposal that arterial BRG was a predictor of hemodynamic outcome during VT, sympathetic nerve activity (SNA), BP and central venous pressure were measured in 14 patients during nitroprusside (NTP) infusion and during rapid VP, simulating VT. Arterial BRG was defined as the slope of the relationship of change in SNA (%) to change in diastolic BP during NTP. BP recovery during sustained VP was defined as the change in BP from the nadir to steady state during sustained pacing. We found that arterial BRG correlated positively with mean BP recovery (r=0.57) (See FIG. 6). FIG. 6 depicts the relationship of recovery of MAP during VP to arterial baroreflex sympathetic gain estimated during NTP infusion. Recovery of MAP was determined as a change in MAP from nadir at onset of pacing to steady-state level after 1 minute of pacing. Recovery of MAP correlated positively with arterial baroreflex gain (r=0.57, P−0.034) and diastolic arterial pressure is references as DAP.

While the above 2 studies evaluated the SNA changes during simulated SVT and VT, the SNA response during VF and rapid VT with CL<240 ms, remain unknown.

Analysis of the changes in sinus node cycle length (SNCL) during VF inductions in patients undergoing the implantation of a defibrillator incorporating an atrial lead provides a unique opportunity to assess the autonomic changes that accompany VF. The purpose of this study was to assess whether the arterial baroreflex, as measured by arterial baroreflex gain (BRG), was a predictor of the change in SNCL during VF and of BP recovery following successful defibrillation. We believed that SNCL changes during VF would correlate with arterial BRG, i.e., the greater the arterial BRG is, the greater the shortening in SNCL during VF. Arterial BRG was measured using the modified Oxford technique in 18 patients referred for the implantation of a defibrillator incorporating an atrial lead. The average SNCL was measured during the 5 seconds prior to VF induction and the last 5 seconds during VF before defibrillation. Percent SNCL change (%ΔSNCL) was determined.

Arterial BRG ranged between −3 and 18 ms/mmHg. During VF, SNCL shortened in 11 patients (Group A, mean %ΔSNCL=−15%), and surprisingly lengthened in 7 patients (Group B, mean %ΔSNCL=5%). There was no correlation between %ΔSNCL and arterial BRG gain (r=0.25, p=0.32). In fact, arterial BRG in Group A was lower when compared to Group B (p=0.075). Sample tracings showing SNCL shortening and lengthening during VF are provided in FIGS. 7 and 8A-8B.

Figure 7:
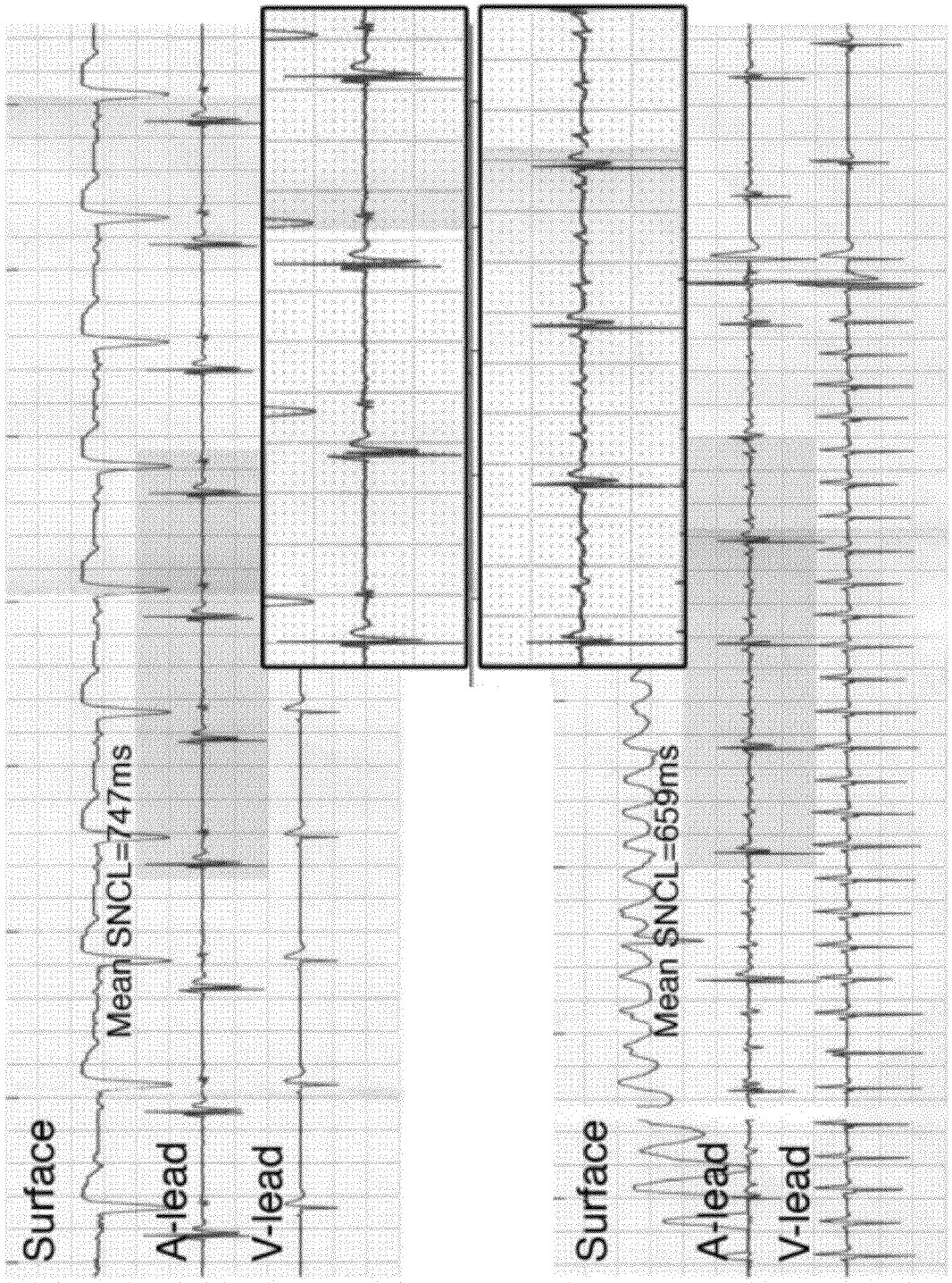
FIG. 7 depicts an upper depicting normal sinus rhythm with a sinus node cycle length (SNCL) equal to about 747 ms and a lower panel during VF, the mean SNCL decreased to 659 ms.

FIG. 7 depicts, in the upper panel, the normal sinus rhythm with a SNCL equal 747 ms. In the lower panel, FIG. 7 depicts, during VF, the mean SNCL decreased to 659 ms. For each panel, from top to bottom; surface ECG, atrial (A) signal, ventricular (V) signal, timing markers are illustrated, and the highlighted segment of the atrial signals are enlarged.

Figure 8A:
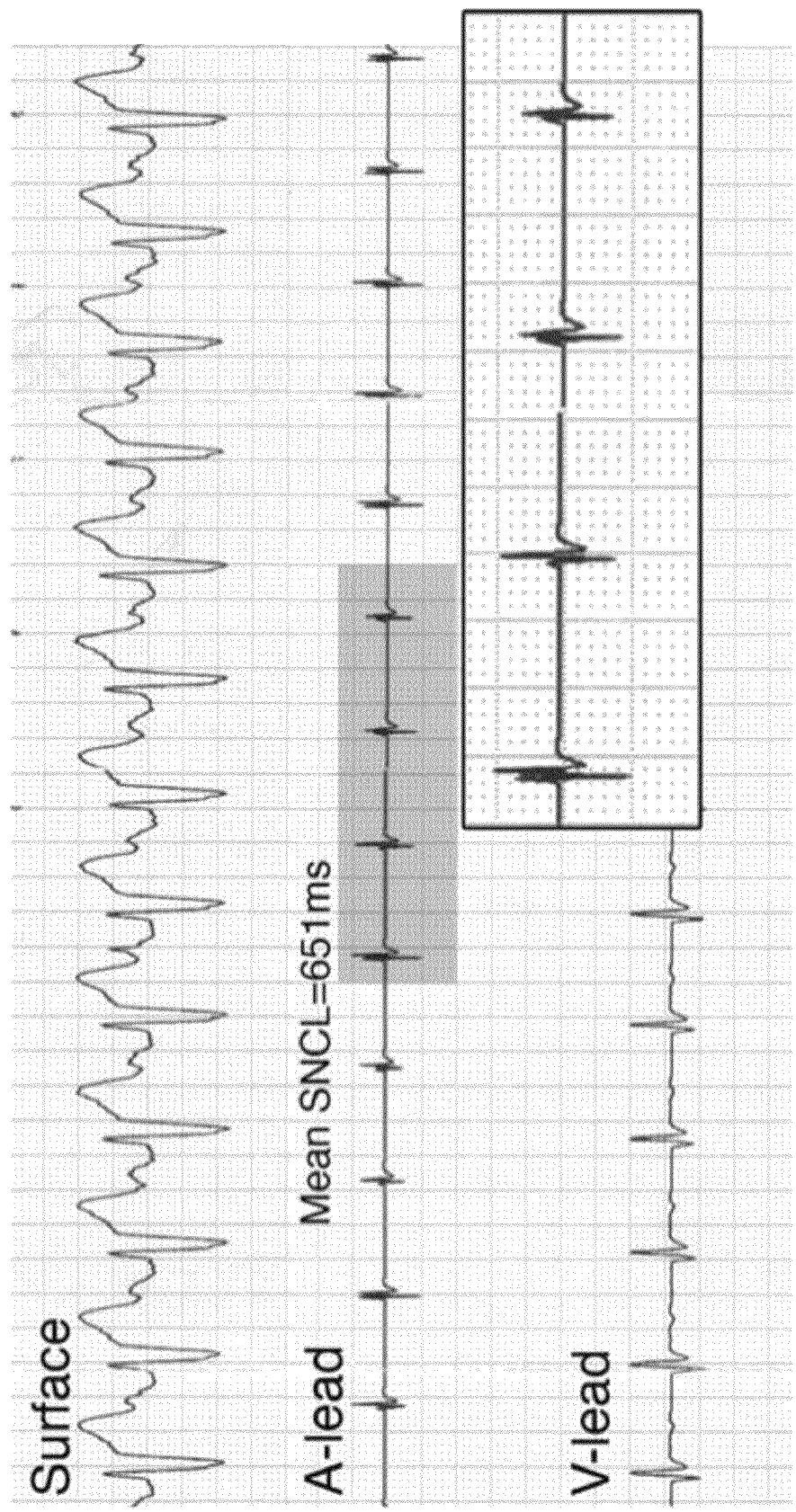
FIG. 8A depicts a normal sinus rhythm with a mean SNCL equal to about 651 ms.
Figure 8B:
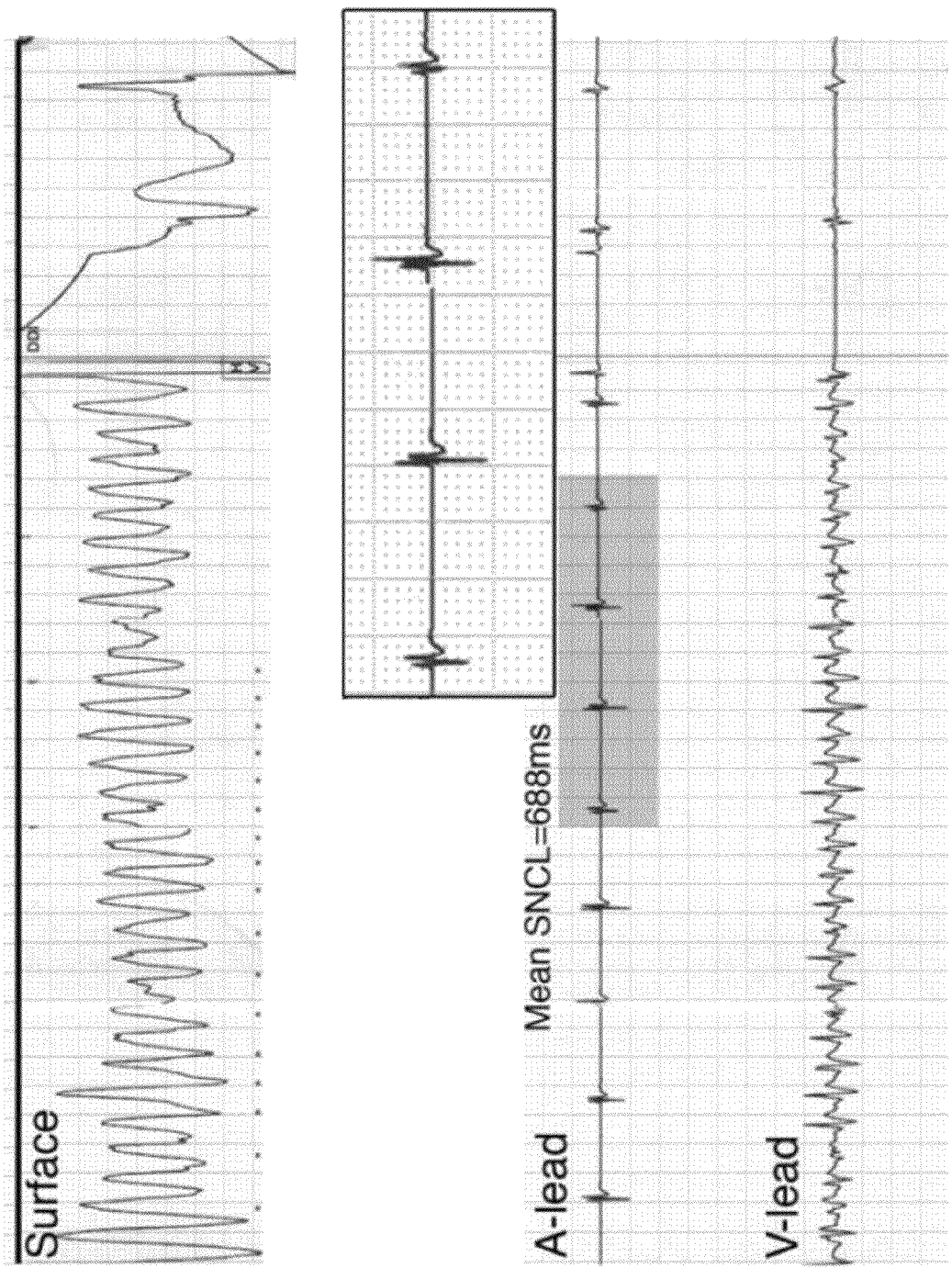
FIG. 8B depicts, during VF, the mean SNCL having increased to about 688 ms.

FIG. 8A depicts the normal sinus rhythm with a mean SNCL equal to 651 ms. FIG. 8B depicts, during VF, the mean SNCL did not decrease but rather increased to 688 ms. For each figure, from top to bottom, surface ECG, timing markers, atrial (A) signal, ventricular (V) signal are provided. The highlighted segments of the atrial signals are enlarged.

This recent study highlights a significant new finding: SNCL lengthening during VF in almost 40% of the patients. The mechanisms underlying the SNCL changes and the clinical implications are unknown. Furthermore, whether the same findings occur with rapid VT with CL<240 ms remain unclear.

It is believed that, with respect to the mechanisms of SNCL changes during FVA, changes in SNCL during FVA are vagally mediated. A test was conducted in a swine model where SNCL changes will be measured during VF and RVP before and after selective parasympathetic, sympathetic and complete autonomic blockade.

Figure 9:
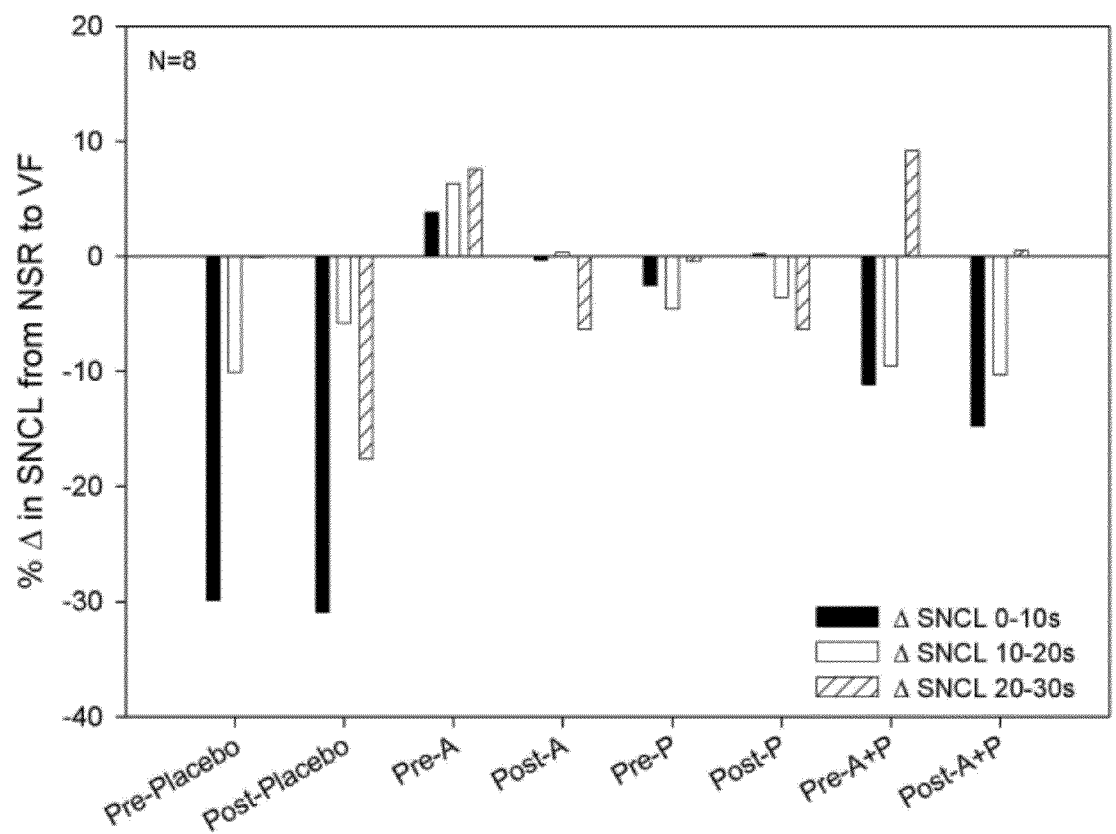
FIG. 9 depicts the percent change in SNCL from baseline at baseline and following the administration of placebo, atropine (A), propranolol (P) and atropine in addition to propranolol (A+P).

In 8 anesthetized pigs, the chest was opened and the heart was exposed on a pericardial cradle. An atrial lead was placed over the right atrial appendage and an arterial catheter in the right femoral artery for BP monitoring. Using DC current or the shock-on-T method, VF was induced and sustained for 30 seconds before applying a DC shock. Following a 10 minute recovery period, atropine (A, n=2) at 0.04 mg/kg, propranolol (P, n=2) at 0.2 mg/kg, both (A+P, n=2) or neither (Placebo, n=2) were administered at random, and VF was re-induced. SNCL changes were assessed before and after drug/placebo administration. Percent SNCL change (%ΔSNCL) was defined as %ΔSNCL=(VF-SNCL−Baseline-SNCL)/(Baseline-SNCL)*100. Atropine administration reversed the SNCL lengthening observed in the 2 pigs while propranolol had no effect on SNCL shortening observed in the 2 other pigs. FIG. 9 depicts the %ΔSNCL at baseline and following the administration of placebo, atropine (A), propranolol (P) and atropine in addition to propranolol (A+P). Our findings suggest that the SNCL changes during the first 30 seconds of VF appear to be vagally mediated.

While the study above is assessing the mechanism of SNCL changes during FVA, the relationship between these changes and peripheral sympathetic activity remain unknown. It is believed that the lengthening and shortening in SNCL are associated with a decrease and an increase in peripheral sympathetic activity respectively. A test was conducted in patients undergoing the implantation of dual chamber ICDs or a generator change. Using the microneurography technique described above, muscle SNA and the SNCL changes during VF inductions and RVP were recorded.

Patients receiving dual chamber ICD implants with defibrillation threshold testing were asked to enroll. SNA recordings were attempted in all patients. In addition, the mean SNCL was measured during the 5 seconds preceding VF onset and the last 5 seconds before defibrillation. Successful SNA recordings were obtained in 3 patients. Sympathoinhibition was observed during VF in 2 patients while sympathoexcitation was noted in the remaining patient. FIGS. 11A-11C show a muscle SNA recording from one of the patients who developed sympathoinhibition during VF. Almost complete sympathetic shut down was noted when compared to baseline. SNCL did not change and even lengthened by 3% in the patient with sympathoinhibition whereas it shortened by 13% in the patient with sympathoexcitation. Our findings of sympathoinhibition associated with SNCL lengthening suggest the presence of vasovagal like physiology during VF in a subgroup of patients.

Figure 12:
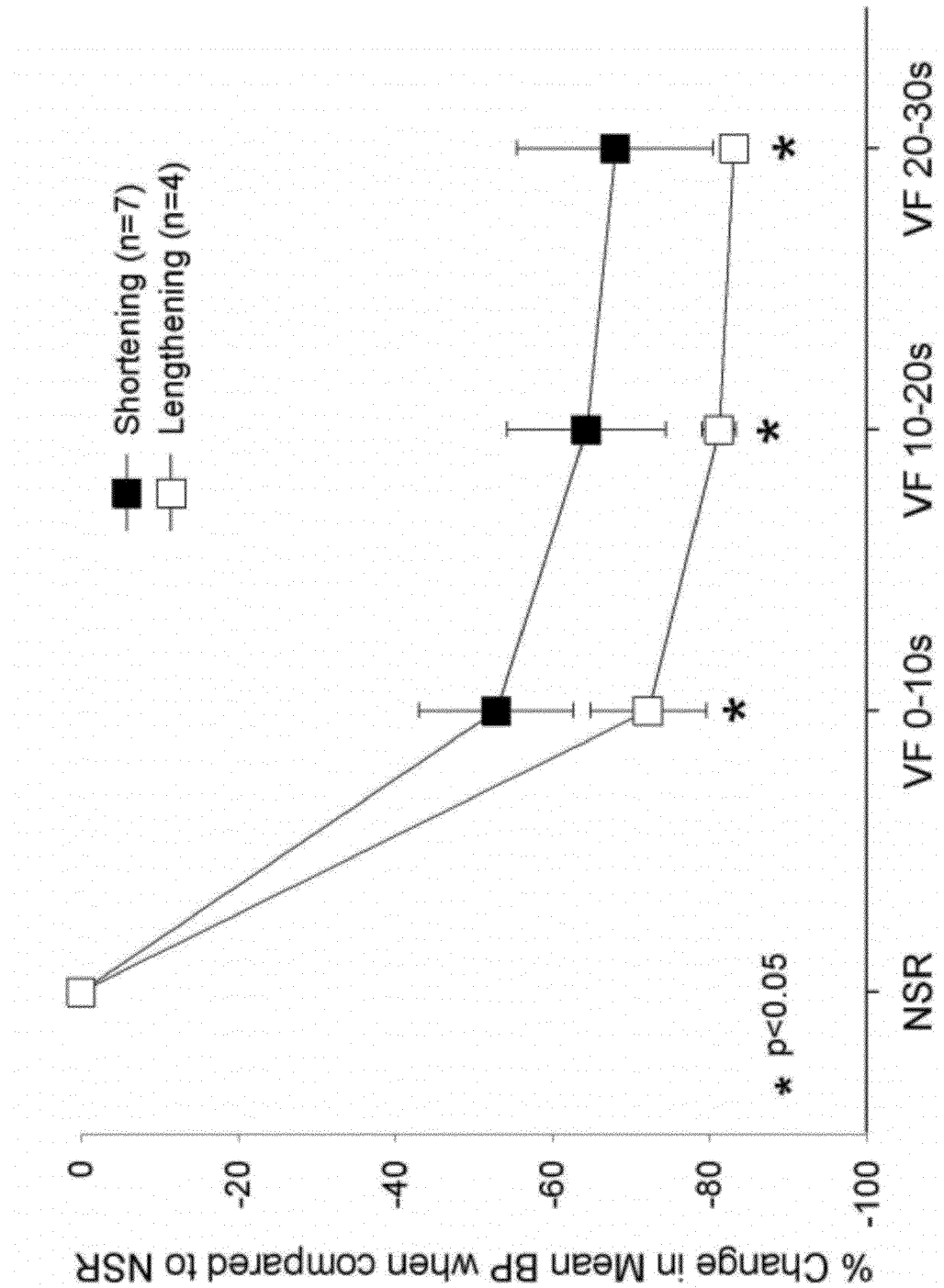
FIG. 12 depicts changes in MBP when compared to NSR during 10-second increments of a 30-second period of AF.

We also sought to determine the role of the autonomic changes during FVA in predicting blood pressure response and time to symptoms' onset. A test was conducted to determine that SNCL lengthening during FVA is associated with a greater decrease in blood pressure when compared to those with SNCL shortening. In 11 anesthetized pigs, the chest was opened and the heart was exposed on a pericardial cradle. A 247-electrode sock was placed around the ventricles, an atrial lead over the right atrial appendage and an arterial catheter in the right femoral artery for blood pressure monitoring. Using DC current or the shock-on-T method, VF was induced and sustained for 30 sec. before applying a DC shock. Animals were divided in to 2 groups based on SNCL response during VF: Shortening group (n=7, %ΔSNCL=−17%), Lengthening group (n=4, %ΔSNCL=4%). In the Shortening group, mean BP fell by 53% in the first 10 sec. when compared to NSR and continued to fall to 64% and 68% at 20 sec. and 30 sec. respectively. In the Lengthening group, BP fell by 72%, 81% and 83% when compared to baseline. The differences in percent decrease in BP between the groups were statistically significant at all 3 time points during VF (p<0.05). SNCL lengthening was associated with a greater decrease in BP when compared to SNCL shortening. The above findings suggest that SNCL changes during VF might be helpful in predicting the magnitude of the hemodynamic fall in BP. Such information could be useful in deciding who has "time" for painless therapy before delivering shock therapy in patients with dual chamber ICDs. SNCL lengthening was associated with a greater decrease in BP when compared to SNCL shortening. FIG. 12 depicts changes in MBP when compared to NSR during 10-second increments of a 30-second period of AF.

Figure 13:
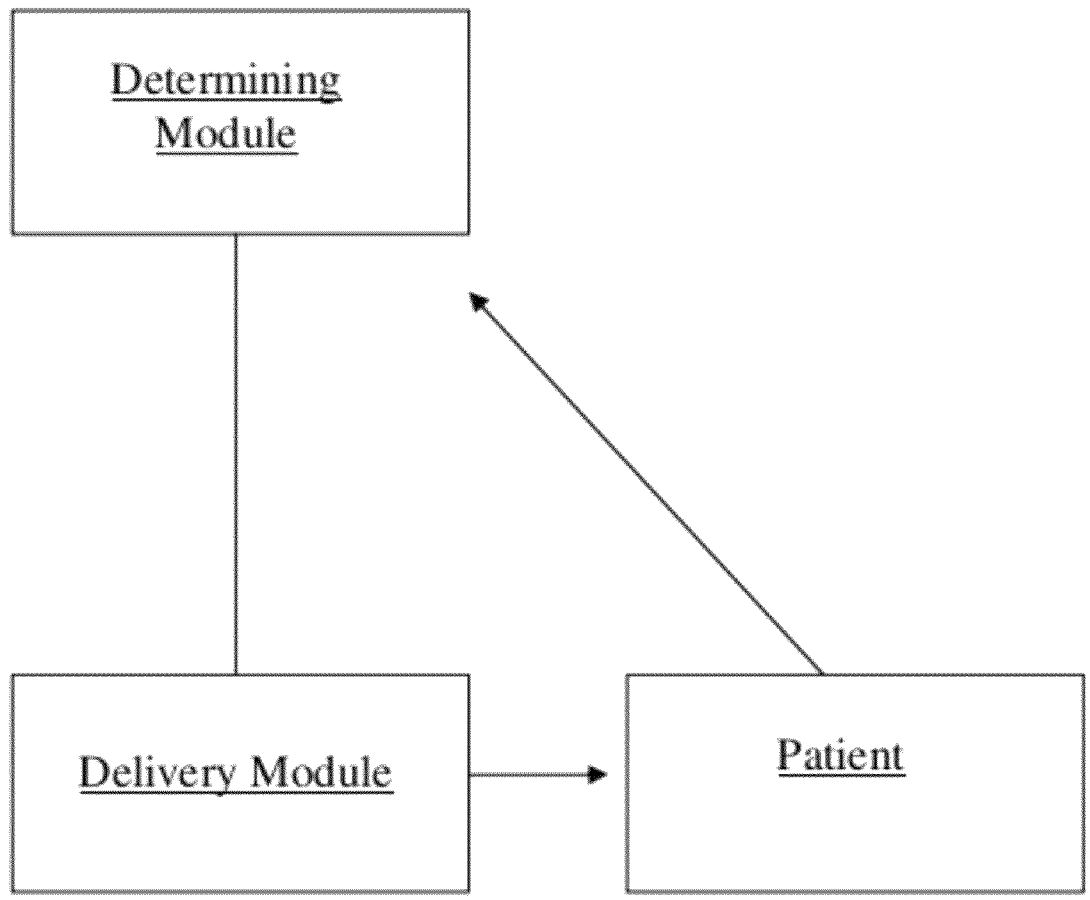
FIG. 13 depicts a determining module in connection with a delivery module, in accordance with embodiments described herein.

FIG. 13 depicts a determining module that can, for example, determine a value of a parameter indicative of a rate of an intrinsic pacemaker of a heart of a patient experiencing a FVA. Also depicted is a delivery module, programmed to deliver a first therapy, for terminating the FVA, to the patient if the value indicates the depolarization rate is about equal to or higher than a threshold, and to deliver a second therapy, for terminating the FVA, different from the first therapy, to the patient if the value indicates the depolarization rate is lower than the threshold. In some embodiments, the determining module receives information from the patient, as indicated in FIG. 13. FIG. 13 also delivery of therapy from the delivery module to the patient.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A method, of treating a fast ventricular arrhythmia, comprising:
   determining a value of a parameter indicative of a rate of an intrinsic atrial pacemaker of a heart of a patient experiencing a fast ventricular arrhythmia (FVA);
   if the value indicates the rate is equal to or higher than a threshold, delivering a first therapy to the patient for terminating the FVA; and
   if the value indicates the rate is lower than the threshold, delivering a second therapy, different from the first therapy, to the patient for terminating the FVA,
   wherein the first therapy comprises anti-tachycardia pacing, and the second therapy comprises at least one of defibrillation and electrical cardioversion.

2. The method of claim 1, wherein the intrinsic pacemaker comprises the sinoatrial node of the patent.

3. The method of claim 2, wherein the parameter indicative of the rate comprises a sinus node cycle length.

4. The method of claim 1, wherein the fast ventricular arrhythmia comprises ventricular tachycardia.

5. The method of claim 1, wherein the determining comprises analyzing an atrial electrogram of the patient.

6. The method of claim 1, wherein the determining is performed using an electrode positioned in an atrium of the patient.

7. The method of claim 1, further comprising:
   if the value indicates the rate is lower than the threshold, delivering a third therapy, in addition to the second therapy, that stimulates the patient's sympathetic nervous system.

8. The method of claim 7, wherein the third therapy is sufficient to raise an arterial blood pressure in the patient.

9. The method of claim 1, wherein the second therapy stimulates the patient's sympathetic nervous system.

10. A method, of treating a fast ventricular arrhythmia, comprising:
    determining a value of a parameter indicative of at least one of vagal activity and peripheral sympathetic activity in a patient experiencing a fast ventricular arrhythmia;
    if the value is in a range indicating the ventricular arrhythmia is more likely to reflect predominant sympathetic activity than predominant vagal activity, delivering painless therapy to the patient; and
    if the value is outside the range, delivering a second therapy, comprising at least one of defibrillation and electrical cardioversion, to the patient,
    wherein the parameter comprises an indicator of a rate of an intrinsic atrial pacemaker in the patient's heart.

11. The method of claim 10, wherein the painless therapy comprises anti-tachycardia pacing.

12. The method of claim 10, wherein the determining and the delivering are performed by a device implanted in the patient.

13. The method of claim 10, wherein the intrinsic pacemaker comprises the sinoatrial node of the patient.

14. The method of claim 10, wherein the parameter indicative of the rate comprises a sinus node cycle length.

15. The method of claim 10, wherein the determining is performed using an electrode positioned in an atrium of the patient.

16. An implantable cardiac device, for treating a fast ventricular arrhythmia, comprising:

a determining module that determines a value of a parameter indicative of a rate of an intrinsic atrial pacemaker of a heart of a patient experiencing a fast ventricular arrhythmia (FVA); and a delivery module, programmed to deliver a first therapy for terminating the FVA to the patient if the value indicates the rate is equal to or higher than a threshold, and to deliver a second therapy for terminating the FVA, different from the first therapy, to the patient if the value indicates the rate is lower than the threshold, wherein the first therapy comprises anti-tachycardia pacing, and the second therapy comprises at least one of defibrillation and electrical cardioversion.

17. The device of claim 16, wherein the parameter is indicative of a rate of the sinoatrial node of the patient.

18. The device of claim 16, wherein at least one of the first and second therapies is electrical.

\* \* \* \* \*